(12) United States Patent
Langenbacher et al.

(10) Patent No.: US 8,079,256 B2
(45) Date of Patent: Dec. 20, 2011

(54) GAS SENSOR AND METHOD FOR ITS PRODUCTION

(75) Inventors: Markus Langenbacher, Schluchsee (DE); Juergen Hall, Roetenbach (DE); Ulrich Demisch, Freiburg (DE); Peer Loebmann, Gorbrunn (DE)

(73) Assignee: Testo AG, Lenzkirch (DE)

( * ) Notice: Subject to any disclaimer, the term of this patent is extended or adjusted under 35 U.S.C. 154(b) by 650 days.

(21) Appl. No.: 12/224,234

(22) PCT Filed: Feb. 22, 2006

(86) PCT No.: PCT/EP2006/001617
§ 371 (c)(1),
(2), (4) Date: Oct. 27, 2008

(87) PCT Pub. No.: WO2007/098774
PCT Pub. Date: Sep. 7, 2007

(65) Prior Publication Data
US 2009/0145220 A1    Jun. 11, 2009

(51) Int. Cl.
*G01N 27/00* (2006.01)
*H01L 21/02* (2006.01)

(52) U.S. Cl. ....................... 73/335.04; 438/49

(58) Field of Classification Search ............... 73/335.04; 438/49
See application file for complete search history.

(56) References Cited

U.S. PATENT DOCUMENTS

| | | | |
|---|---|---|---|
| 4,393,434 A * | 7/1983 | Imai et al. | 73/335.04 |
| 4,438,480 A * | 3/1984 | Chambaz et al. | 73/335.04 |
| 4,768,012 A | 8/1988 | Williams et al. | |
| 5,143,696 A | 9/1992 | Haas et al. | |
| 6,126,312 A * | 10/2000 | Sakai et al. | 73/335.04 |
| 6,173,602 B1 | 1/2001 | Moseley | |
| 2003/0217586 A1* | 11/2003 | Gouma | 73/31.06 |

FOREIGN PATENT DOCUMENTS

| | | |
|---|---|---|
| EP | 59119253 | 7/1984 |
| EP | 06213851 | 8/1994 |
| JP | 2003130833 A1 | 5/2003 |
| JP | 2003138480 A1 | 5/2003 |

OTHER PUBLICATIONS

K. Chou, T. Lee, and F. Liu, "Sensing mechanism of a porous ceramic as humidity sensor." Sensors and Actuators B, vol. 56 (1999) pp. 106-111.*

O. K., Varghese, D. Gong, M. Paulose, K. G. Ong, C. A. Grimes, E. C. Dickey, "Highly ordered nanoporous alumina films: Effect of pore size and uniformity on sensing performance." J. Mater. Res. vol. 17, No. 5 (May 2002) pp. 1162-1171.*

C. B. Park, et al., "Fabrication of porous polymeric film for humidity sensing", Sensors and Actuators B, vol. 13-14, 1993, pp. 86-88, XP002381374.

* cited by examiner

*Primary Examiner* — Lisa Caputo
*Assistant Examiner* — Punam Roy
(74) *Attorney, Agent, or Firm* — Muirhead and Saturnelli, LLC

(57) ABSTRACT

In a gas sensor with at least two electrodes and with a sensor body which is connected thereto and is composed of a gas-sensitive material, in addition to pores which may already be present, second cavities are provided in the sensor body. The second cavities may be suitable on account of their size to facilitate and accelerate the distribution of gas molecules in the sensor body and to thus improve the time response of the gas sensor.

40 Claims, 5 Drawing Sheets

GAS SENSOR AND METHOD FOR ITS PRODUCTION

TECHNICAL FIELD

This application relates to a gas sensor having at least two electrically conducting layers which form electrodes and having a sensor body connected thereto, which has a gas-sensitive material which measurably changes at least one physical parameter, depending on the prevailing distribution density of a gas which has penetrated, wherein the sensor body has first cavities in the form of pores, and a method for manufacturing such a gas sensor.

BACKGROUND OF THE INVENTION

Gas sensors for detection of various gases are known from the related art in various designs, functionalities, and detection sensitivities. In a gas sensor, after penetration of gas molecules, a sensor body changes its physical properties such as the electrical resistance or the dielectric constant as a function of the distribution density of the gas molecules. This is analyzed in a system having two electrodes by measuring a resistance or an electrical capacitance.

Such sensors are known, for example, from the publication "Integrated multifunctional humidity sensor" by Krutovertsev in *Sensors and Actuators*, Vol. A 62 (1997), 582-585, which describes gas sensors having sensitive layers made of various materials and operating as capacitive or resistive sensors. It also describes how the sensitive layers may be manufactured using sol-gel technology.

U.S. Pat. No. 4,768,012 describes a capacitive gas sensor having a sensor body based on silica, titanium, zirconium or aluminum using sol-gel technology. Furthermore, a temperature sensor is integrated into the sensor for compensating for temperature effects in the measurement.

EP 0 403 994 A1 describes a capacitive gas sensor having a polyetherimide layer as a dielectric. Furthermore, the use of cellulose acetate layers as sensitive layers is also mentioned there.

EP 0 403 994 A1 describes a capacitive moisture sensor, i.e., a sensor for water vapor, which is designed as a capacitor in a layered structure. A moisture-sensitive polymer film is provided as a dielectric between two metallic electrodes, one of which is formed by a moisture-permeable metal layer. Depending on the ambient moisture level, more or less water vapor diffuses into the polymer film, thus having a negative effect on its dielectric constant. Measurements of the capacitance of the capacitor formed by the two metal layers and the polymer film therefore allow inferences about the ambient water vapor level. Using such gas sensors based on polymer films, water vapor is detectable in principle in the range from approximately 0% to 100% relative humidity (RH). However, due to the inadequate water vapor sensitivity of the polymer layers, the measurement range below 1% RH is not accessible with sufficient accuracy for sophisticated measurements.

For this reason, more sensitive porous layers, in particular aluminum oxide layers in the case of water vapor, have been used as gas-sensitive layers for a long time. U.S. Pat. No. 2,237,006 thus describes an electric hygrometer in which aluminum oxide as a water vapor-sensitive layer is situated between two metal layers, one of which is permeable to water vapor in a sensor design having a layered structure. The water vapor content, i.e., the moisture, is determined on the basis of the change in the ohmic resistance of this layer induced due to adsorption of water vapor in the aluminum oxide layer.

In comparison with sensors based on polymers, such gas sensors have an expanded detection range. However, their manufacture, in which the porosity of the metal oxide layers is usually created by anodic oxidation of the metals used, is associated with a high manufacturing cost. In addition, they do not have long-term stability and may be used only in a narrow temperature range. Measuring gas temperatures above 100° C. are therefore not accessible to this generic sensor type.

In addition, a moisture sensor in which the electrodes are situated in a layered configuration is also known from KR 00 23937. The water vapor-sensitive layer is applied there with the aid of sol-gel technology. The manufacture of such gas sensors and/or moisture sensors is simplified in comparison with the use of a moisture-permeable cover electrode, i.e., one that is permeable to water vapor. The measurement range extends in a range from approximately 20% to 90% RH in the case of detection of water vapor by the sensors.

In many application cases, the sol-gel technique is preferred in the manufacture of the gas-sensitive layer, which is referred to by the term "sensor body" in conjunction with the present layer because designs other than the design of a planar layer are also conceivable, although the manufacture of sensor bodies is not limited to this technology.

In this sol-gel technique, a colloidal sol is first formed in principle from inorganic salts, organometallic compounds or alkoxides with organic solvents or water and special compounds, in particular stabilizing additives. This sol may be applied to a substrate by various coating operations. For example, it is converted to an amorphous gel by hydrolysis and condensation reactions. This gel is dried and may additionally be processed thermally, e.g., by pyrolysis. It may then be in its oxidic form.

This technique allows comparatively simple mixing of different components of the gas-sensitive layer such as different metal oxides. Furthermore, through suitable sol components and adequate process management, the porosity of the finished gas-sensitive layer and thus its gas adsorption rate and/or gas sensitivity are regulatable to a certain extent. In conjunction with the large contact surface areas between the gas-sensitive layer and the electrodes adjacent thereto in the layered structure in comparison with the structure of intermeshing electrode combs, this yields a highly sensitive gas sensor, which may be used at an operating temperature of up to 300° C. with much higher measuring gas temperatures than known gas sensors based on anodized aluminum (up to 100° C.) or polymers (up to 200° C.).

The electrical impedance of the porous gas-sensitive layer of the sensor is analyzed when using this gas sensor, as is customary with capacitive sensors. The electrical impedance depends on the concentration of the gas to be detected in the surroundings of the gas sensor and/or the amount of gas adsorbed in the gas-sensitive layer. As an alternative to analyzing the impedance of the gas sensor, there is also the possibility of recording only the changes in capacitance or resistance.

As indicated above, the sol-gel technique to be used allows a comparatively simple variation in the constituents of the gas-sensitive layer and variation of the structure of this layer within certain limits. Therefore, in the practical implementation, the composition and structure of the gas-sensitive layer manufactured by the sol-gel technique are tailored to the gas to be detected and to the desired measurement range. In particular, the gas-sensitive layer may be designed specifically for detection of water vapor. In addition, the gas-sensitive layer is designed specifically for detection of traces of gas, in particular trace moisture, i.e., traces of water vapor.

Examples of constituents of the sol for such a trace moisture sensor include aluminum, silicon, titanium, magnesium, vanadium, zirconium, barium or iron and/or the oxides thereof. In addition, potassium, lithium, carbon, or tin are also possible constituents. Individual metal oxides as well as mixtures of different metal oxides may be used.

It is also possible for the gas-sensitive layer to have an optimized pore size distribution, in particular pore diameters of less than 1 µm on the average. The pore diameter may also be less than 0.3 µm on the average. The layer thickness of the sensor body, if it has the shape of a planar layer, may be a few µm. A gas-sensitive layer having a total layer thickness of less than 1 µm is particularly advantageous.

Regardless of whether the sensor body or the gas-sensitive layer is manufactured by sol-gel technology or as a polymer film, as a metal, metal oxide, or ceramic body, the physical effect is nevertheless based on the diffusion of gas atoms and/or molecules into a solid body. This diffusion process naturally takes a certain amount of time, which determines the response time of the gas sensor. To accelerate the response, it is possible, for example, to make at least one of the electrodes of the gas sensor permeable for the gas to be detected to allow diffusion of the gas molecules from this side over a large area. Nevertheless, it has been found that the response time of such sensors is not as short as desired.

Accordingly, it would be desirable to improve the response time of gas sensors of the type described above.

SUMMARY OF THE INVENTION

According to the system described herein, a gas sensor may be provided that, independently of and, if necessary, in addition to the existence of pores in the sensor body, includes second cavities having the purpose of facilitating and accelerating penetration of the gas to be measured into the sensor body and the distribution of gas molecules in the sensor body. This yields a diffusion equilibrium of the gas in the sensor body within a short period of time in the same way and the response time is shortened accordingly.

Second cavities are thus introduced into the sensor body through appropriate measures in manufacturing, in addition to the pores that are already present to a lesser or greater extent. These cavities are advantageously larger on the average than the average pore size. The term "average pore size" may be understood here to refer first to the statistical mean of the pore size, the maximum of the pore size distribution (e.g., in a Gaussian distribution) or the value of the pore size, of which it may be stated that half of the pores have smaller dimensions while the other half have larger dimensions.

The second cavities therefore allow a rapid migration of the gas molecules within the sensor body, in particular due to their size, and on the whole increase the surface area of the sensor body through which the gas molecules may penetrate. This reduces the effective path length which the gas molecules must travel within the body until achieving a uniform distribution within the sensor body.

It may be advantageous in particular if the second cavities open into one of the delimiting surfaces of the sensor body, because in this way, this area is roughened to a certain extent and the effective exposure area for the gas molecules is increased significantly. The gas molecules may enter the interior of the sensor body in the gas space to a certain extent and may reach the internal regions of the sensor body relatively rapidly due to diffusion in the solid body after penetrating into the actual body.

The second cavities may be created by a thermal treatment of the sensor body, for example. This may include sudden temperature changes, for example, which create cracks in the sensor body. However, it is also conceivable that cavities are created solely due to great temperature fluctuations and the corresponding thermal stresses.

Furthermore, it is possible to provide for a space-demanding substance to be added to the material of the sensor body and then removed by dissolving, etching, vaporizing or diffusion in a subsequent step or by dissolving, etching, vaporizing or diffusion after reacting chemically with another substance. For example, a low-volatility organic substance may be oxidized in atmospheric oxygen at high temperatures and may then leave the layer in the form of carbon dioxide. The added substance may be a solvent, for example. This forms a rougher porosity in the sensor body in particular. A spongy open-pored consistency of the sensor body may be achieved in this way.

The sensor body may also be embrittled by a temperature treatment or by irradiation with electromagnetic radiation or particulate radiation, e.g., in the form of $\alpha$-, $\beta$- or $\gamma$-radiation, by laser treatment or structuring using UV radiation, and then exposed to a mechanical or thermal stress to create cracks. Removal of parts of the sensor body by evaporation, sputtering or similar techniques may also take place directly through irradiation.

It may also be possible to provide for embrittlement of the sensor body by diffusion of solvents out of it, but also by irradiation. After embrittlement, there is an increased risk of cracking due to mechanical or thermal stresses; this is usually undesirable in the industry but is utilized in a targeted manner in the system described herein.

Finally, the sensor body may also be manufactured by foaming a material that already has initial cavities in the form of pores. The body is then solidified after foaming.

The sensor body may also be made by compression or sintering of particles of a material that already has pores. For example, it is conceivable that a sensor body is produced first with the help of the known sol-gel technology, then is ground and the resulting fine particles are next pressed to form a body. The resulting interspaces between the particles may then be approximately as large as the individual processed particles.

Essentially, the sensor body may be made of a material produced by the sol-gel technique, but also at least partially from a polymer, a metal oxide or a ceramic. Examples of corresponding materials include polyetherimide, cellulose acetates, polyimides, polysulfones, $Al_2O_3$, $SiO_2$.

Mixtures of the aforementioned components may also be used to adjust certain properties of the sensor body such as a sensitivity for certain gases to be detected.

With regard to the size of the second cavities, they are at least twice as large as the average size of the pores (first cavities) in at least one direction of extent, advantageously being five times larger and particularly advantageously at least 10 times larger. The shape of the cavities is preferably that of a gap or crack or there may also be a labyrinthine connection between the second cavities. The first cavities may be at least twice as large as the gas molecules to be detected, and the second cavities are advantageously five times as large as the gas molecules.

In at least one direction of extent, the first cavities may be larger than 0.5 nm in absolute units of measurement. The second cavities may be larger than 2.5 nm in at least one direction of extent, advantageously larger than 5 nm. In one direction, they may advantageously extend over a distance corresponding to at least half the layer thickness of the sensor body or even 70% of the layer thickness.

The number and size of pores in the sensor body may be so great that its porosity is more than 15%. As a result of all these measures, the diffusion of gas molecules into the sensor body and within the sensor body is increased.

To create second cavities in the sensor body, instead of or as an alternative to the measures otherwise mentioned, it is also possible to provide for a mechanical effect to act on the sensor body. This may be accomplished, for example, by embossing, grinding, scratching, drilling, punching, heavy shaking or bending.

According further to the system described herein, a sensor of the type defined initially may include a sensor body which has a gas-sensitive material in the form of a polymer, a metal, a metal oxide or a ceramic. The approach according to the system described herein may be achieved merely through the presence of second cavities, which are at least partially interconnected in an open-pored spongy structure, for example. These cavities allow rapid diffusion of the gas molecules and rapid achievement of a diffusion equilibrium in the sensor body. The second cavities may be produced by one of the machining methods mentioned above and/or may also correspond to the above-mentioned size ratios.

In addition, in the gas sensor according to the system described herein, an insulation layer may advantageously be provided between the electrodes in addition to the sensor body. This may be used to advantageously adjust the total impedance of the gas sensor thereby formed via the insulator if it is used as a capacitive sensor. The insulation layer may also function as a barrier and protection for the basic electrode in aggressive environments and may thus increase the long-term stability of the sensor.

Since the electrical values of the sensor body depend not only on the distribution density of the gas molecules but usually also on the temperature, the measured values thereby detected may also be corrected with respect to the prevailing temperature, depending on the required measuring accuracy. For this reason, integration of a temperature sensor into the gas sensor is advantageous because it facilitates the correction of measured values and allows the measurement to be performed directly on the sensor, thereby also increasing the accuracy of the temperature measurement.

The sensor may also be provided with a heating element or a cooling element to adjust a desired measuring temperature via temperature regulation or, for example, to at least prevent condensation from forming on the sensor. It is also possible to provide for the sensor to be baked out by the heating element from time to time to thereby obtain data about the prevailing status of the sensor.

According further to the system described herein, a method for manufacturing a gas sensor may include first applying an initial electrode to a substrate, e.g., by vapor deposition; the substrate may be vitreous or ceramic and the first electrode may be made of gold, for example. A sensor body may then be applied to the electrode, e.g., in the form of a sol-gel, which may then be subjected to the conventional procedure for solidification of the sol-gel. The sensor body is then treated in the manner described above to create second cavities, and in a subsequent step, a second electrode is applied, e.g., again by vapor deposition. One of the two electrodes may be designed to be gas permeable, for example, to accelerate the penetration of gas into the sensor body. Otherwise the gas to be detected may also penetrate into the exposed interfacial areas of the sensor body, which are not covered by the electrodes.

BRIEF DESCRIPTION OF THE DRAWINGS

Embodiments of the system described herein are explained in greater detail below with reference to figures that are briefly described as follows.

DETAILED DESCRIPTION OF VARIOUS EMBODIMENTS

Figure 1:
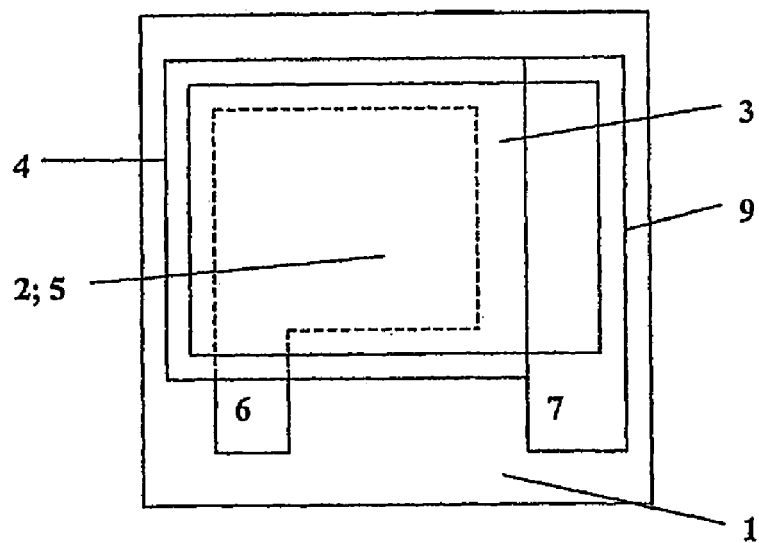
FIG. 1 shows a schematic diagram of a top view of a gas sensor according to an exemplary embodiment of the system described herein (sandwich design).
Figure 2A:
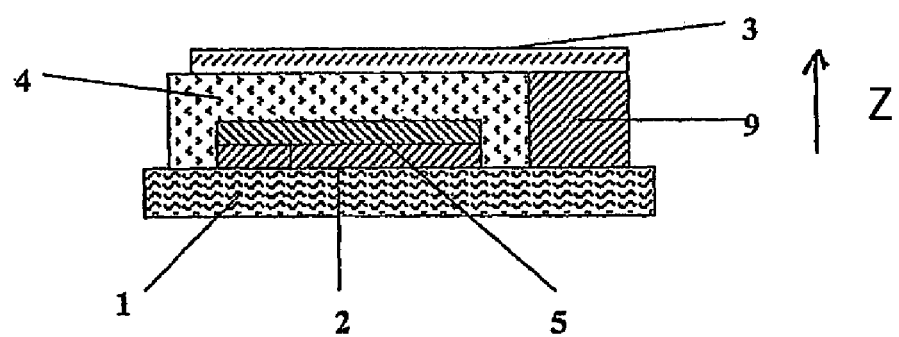
FIG. 2a shows a cross section through the schematic diagram of the gas sensor from FIG. 1.

The schematic diagrams in FIG. 1 and FIG. 2a show an outline diagram of an exemplary embodiment of a gas sensor according to the system described herein and a cross section through same, respectively. A first conductive layer 2, which is applied in particular by vapor deposition and/or sputtering of metal, is provided on substrate 1 as the first electrode. On this first electrically conducting layer 2, an insulator layer 5 is optionally provided, preventing diffusion of molecules of the gas to be detected out of gas-sensitive layer 4 to first conductive layer 2 and thereby protecting it from ambient influences. In addition, the total impedance of the gas sensor is adjusted in the desired manner through insulator layer 5. The sensor body in the form of a gas-sensitive layer 4 is produced and applied by the sol-gel technique described above. Directly adjacent to gas-sensitive layer 4 at the side, a reference electrode 9 is situated on substrate 1. It is connected to the second electrode in the form of second electrically conducting layer 3, which is at least partially permeable for the gas to be detected.

As FIG. 1 shows, the first electrically conducting layer and the reference electrode protrude partially above the other layers of the gas sensor, so that these protruding areas are available as a contacting area 6 for first electrically conducting layer 2 and/or as contacting area 7 for second electrically conducting layer 3. These contacting areas are directly adjacent to the surface of substrate 1, which is typically made of glass or a ceramic material, so that it is advantageously contactable by soldered sensor pins.

During operation of the gas sensor, molecules of the gas to be detected diffuse through open side faces of the gas-sensitive layer or through the at least partially gas-permeable second electrode 3 into gas-sensitive layer 4, where they are adsorbed. The complex impedance (capacitance and/or ohmic resistance) of gas-sensitive layer 4 is influenced in this way. Changes in these material properties are detected by measuring the impedance of the capacitor formed by electrically conducting layers 2 and 3 and by gas-sensitive layer 4 and insulator 5 and allow conclusions to be drawn regarding the gas concentration in the environment.

The constituents and the structure of sensor body 4 formed from the gas-sensitive layer are to be adapted to the gas to be detected and to the desired measurement range, as indicated above.

Figure 2B:
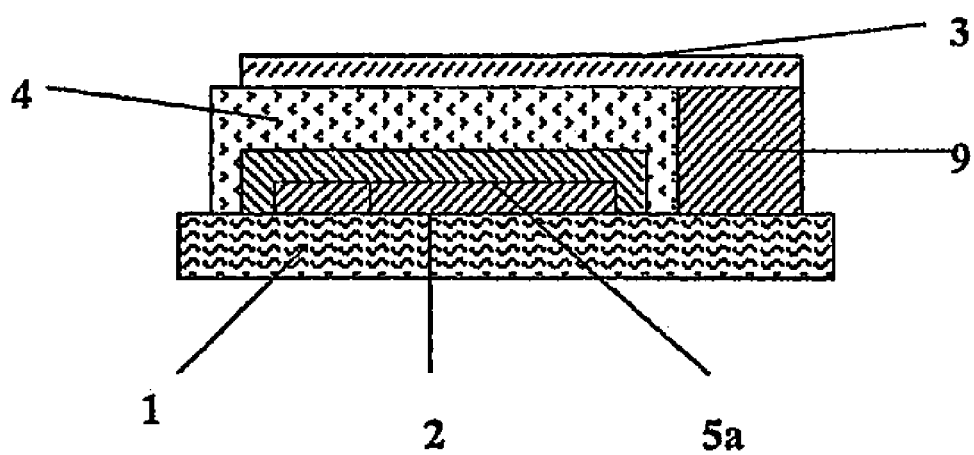
FIG. 2b shows a cross section through a gas sensor in which the insulator layer is designed so that it surrounds the first conductive layer according to an embodiment of the system described herein.

FIG. 2b shows an alternative embodiment variant of a gas sensor according to the system described herein in which insulator layer 5a is designed to also surround first electrode 2 on its side faces. Protection of the first electrode against ambient influences is increased in this way.

Figure 3A:
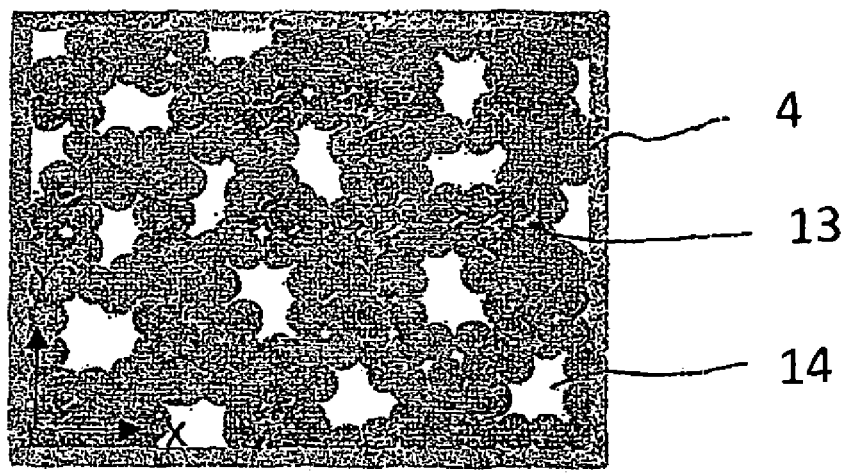
FIG. 3a shows a section through the sensor body having first and second cavities according to an embodiment of the system described herein.

FIG. 3a shows schematically and in detail a section in direction x-y through a sensor body 4, the first electrode, the sensor body and the second electrode to be imagined as lying one on top of the other in the z direction. Dark areas represent regions filled by material manufactured by a sol-gel technology, for example, having small pores 13, shown as light areas in between.

In addition, larger white areas are also shown, which form second cavities 14 and have a shape differing from the shape of the pores, e.g., an asymmetrical shape. These may be formed, e.g., by thermal processing of the sol-gel layer, which creates corresponding recesses due to thermal stresses in the layer and loss of solvents. However, they may also be produced by adding a so-called sacrificial chemical, e.g., an organic component, to the starting sol, whereupon then the sol-gel layer is produced by draw-coating or spin-coating and then the sacrificial chemical is evaporated by thermal processing of the layer.

It is also conceivable to act on the sol-gel layer mechanically even after thermal processing thereof, e.g., to form additional openings in the layer through embossing. This may be followed by additional thermal processing, solidifying the resulting structure having second cavities and pores.

Figure 3B:
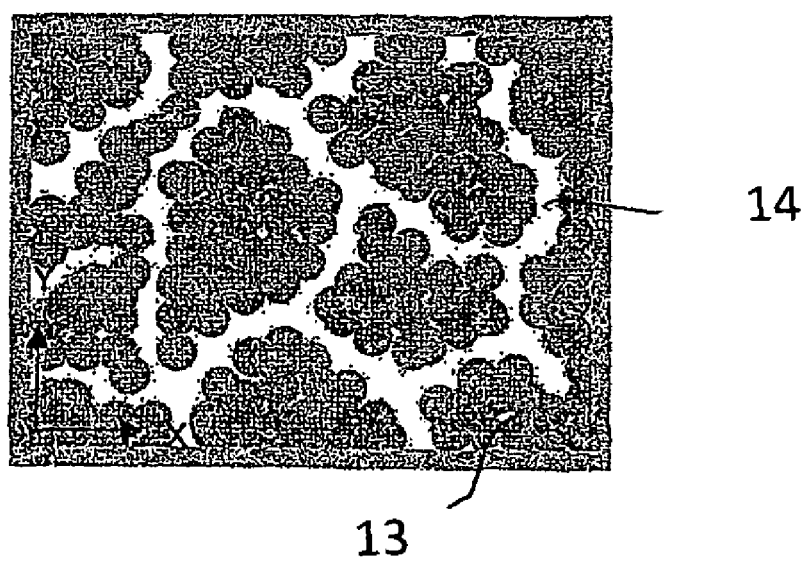
FIG. 3b shows a section through a sensor body having first cavities and second cavities in the form of labyrinthine cracks according to an embodiment of the system described herein.

As in FIG. 3a, FIG. 3b shows a section through a sensor body, wherein the second cavities are formed as continuous cavities and form a labyrinthine crack structure propagating continuously even in the z direction.

Figure 4:
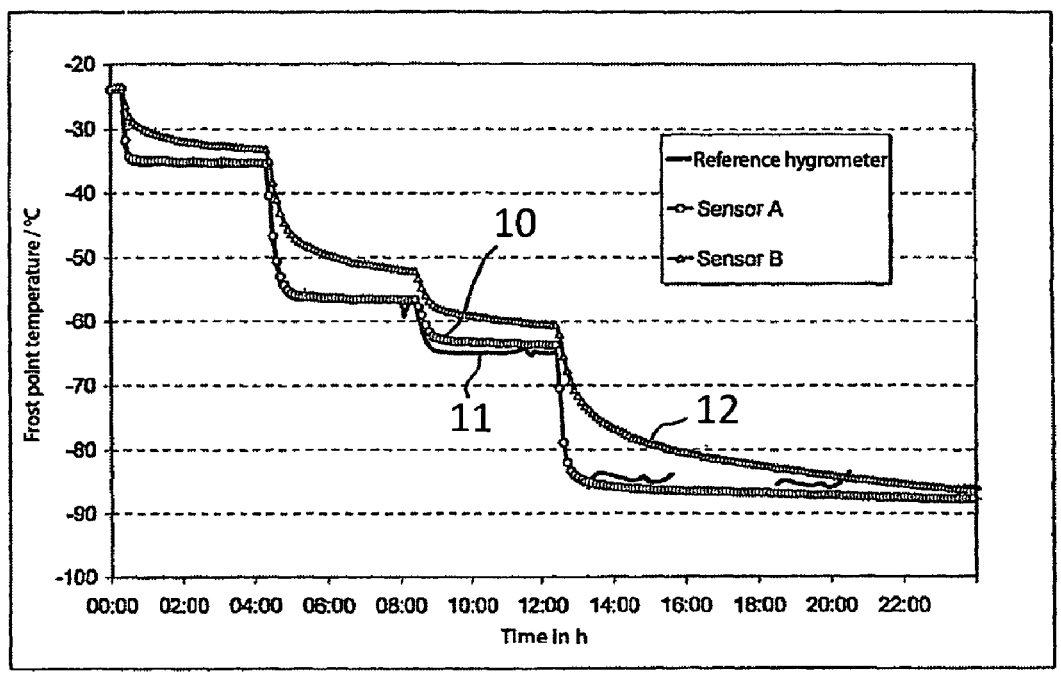
FIG. 4 shows a diagram of the response time of the gas sensor according to an embodiment of the system described herein.

FIG. 4 shows a measurement of the frost point temperature in degrees Celsius plotted on the y-axis as a function of time, with the moisture to be measured changing over time. The frost point temperature is clearly related functionally to the atmospheric humidity to be measured, which is to be detected by the gas sensor.

The graph shows merely that with changes in atmospheric humidity, the measurement by the reference hygrometer, represented by curve 11, with the qualified measured values, follows directly the altered humidity. Like the measured values of the reference hygrometer according to curve 10, the value detected by the gas sensor designed according to the present invention follows the altered humidity values with a short response time.

However, curve 12 shows that a conventional gas sensor according to the related art has a much slower response time to changes in humidity.

Figure 5:
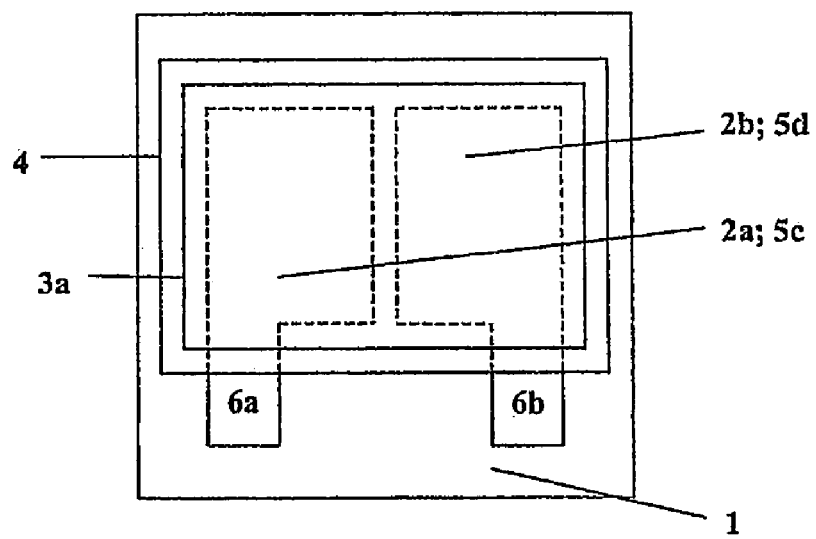
FIG. 5 shows a schematic diagram of a top view a gas sensor according to another exemplary embodiment of the system described herein (butterfly design).

FIG. 5 shows a schematic diagram of a view from above of another exemplary embodiment of a gas sensor according to the system described herein in the so-called butterfly design. This is again a gas sensor including a capacitor in layered design, but instead of two electrically conducting layers 2a, 2b and 3a as previously, now three such layers are provided, electrically conducting layer 3a, which is connected to the surroundings according to the sectional diagram in FIG. 6, being at least partially permeable for the gas to be detected. Electrically conducting layers 2a, 2b, 3a are spaced a distance apart, sensor body 4 being between them in the form of a gas-sensitive layer manufactured by the sol-gel technique, its composition and structure being in turn based on the gas to be detected and the expected measurement range. Similarly to the preceding exemplary embodiments, insulator layers 5c and 5d are provided on electrically conducting layers 2a and 2b. To increase the mechanical stability of the gas sensor, insulating substrate 1 is also provided in this exemplary embodiment.

The advantage of this embodiment variant is that electrically conducting layer 3a, referred to as the cover electrode and being in contact with the external surroundings, need not be contacted. The capacitor on which the gas sensor is based is formed here by two electrodes in the form of electrically conducting layers 2a and 2b as well as insulator layers 5c and 5d between them and gas-sensitive sol-gel layer 4. Therefore, a reference electrode 9, like that indicated in FIGS. 1, 2a and 2b, may be omitted.

Instead, two electrically conducting layers 2a and 2b are designed so that they protrude above the other layers of the gas sensor, the protruding areas being available as contacting areas 6a and 6b for particular electrically conducting layer 2a or 2b. As indicated by FIG. 5, these contacting areas 6a and 6b are directly adjacent to the surface of substrate 1, so that they may again be contacted advantageously via soldered sensor pins.

Figure 6:
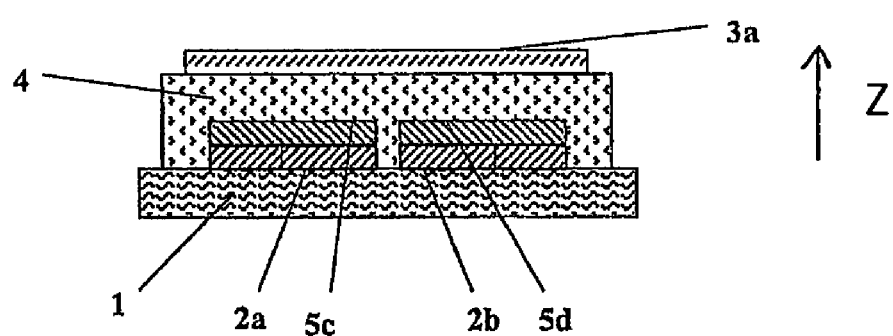
FIG. 6 shows a cross section through the schematic diagram of the gas sensor from FIG. 5.

Simpler contacting of the gas sensor according to the system described herein is possible in this way because cover electrode 3a need not be contacted. In comparison with the gas sensors shown in FIG. 2a or 2b, however, the result for the gas sensor in FIG. 6 is a capacitance which amounts to only approximately one-fourth the capacitance of a gas sensor from FIG. 2a or 2b if electrically conducting layers 2a and 2b taken together cover an area of substrate 1 approximately as large as electrically conducting layer 2 and if insulation layers 5, 5a, 5c and 5d as well as gas-sensitive layer 4 are each approximately of the same thickness. The resulting reduced sensitivity of such a gas sensor may be compensated, however, by an appropriate correction of the dimensions of the various layers of the gas sensor from FIG. 6.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A gas sensor, comprising:
    at least two electrically conducting layers which form electrodes; and
    a sensor body connected thereto, the sensor body including a gas-sensitive material which changes at least one physical parameter depending on the distribution density of a penetrating gas prevailing therein, the sensor body having first cavities in the form of pores and second cavities which have at least one of: a different shape from the first cavities and a different size that is larger in at least one direction of extent on the average in comparison with an average size of the first cavities, wherein the quotient of pore volume and sensor body volume (porosity) is greater than 15%.

2. The gas sensor as recited in claim 1, wherein the sensor body includes at least one of: a sol-gel material, a polymer, a metal oxide and a ceramic.

3. The gas sensor as recited in claim 1, wherein the second cavities open into at least one of the delimiting surfaces of the sensor body, which are provided for penetration of molecules of a gas that is to be detected.

4. The gas sensor as recited in claim 1, wherein the size of the second cavities in at least one direction of extent is at least twice as great as the average size of the first cavities.

5. The gas sensor as recited in claim 4, wherein the size of the second cavities in at least one direction of extent is at least five times greater than the average size of the first cavities.

6. The gas sensor as recited in claim 5, wherein the size of the second cavities in at least one direction of extent is at least ten times greater than the average size of the first cavities.

7. The gas sensor as recited in claim 1, wherein the size of the first cavities is at least twice as great as the size of the molecules of the gas to be detected.

8. The gas sensor as recited in claim 1, wherein the size of the second cavities is at least five times greater than the size of the molecules of the gas to be detected.

9. The gas sensor as recited in claim 1, wherein the size of the first cavities in at least one direction of extent is greater than 0.5 nm.

10. The gas sensor as recited in claim 1, wherein the size of the second cavities in at least one direction of extent is greater than 2.5 nm.

11. The gas sensor as recited in claim 1, wherein the extent of the second cavities in at least one direction amounts to at least 50% of the layer thickness of the sensor body.

12. The gas sensor as recited in claim 1, wherein the second cavities form an open-pored spongy structure.

13. The gas sensor as recited in claim 1, further comprising: an insulation layer situated between the electrodes in addition to the sensor body.

14. The gas sensor as recited in claim 1, further comprising: at least one of: a temperature sensor, a heating element and a cooling element integrated into the gas sensor.

15. A gas sensor, comprising:
at least two electrically conducting layers which form electrodes; and
a sensor body connected thereto, the sensor body including a gas-sensitive material which changes at least one physical parameter in a measurable manner depending on the distribution density of a penetrating gas prevailing therein, the sensor body having first cavities in the form of pores and second cavities which are formed by different measures or physical effects than the pores during the production of the sensor body, wherein the quotient of pore volume and sensor body volume (porosity) is greater than 15%.

16. The gas sensor as recited in claim 15, wherein the sensor body includes at least one of: a sol-gel material, a polymer, a metal oxide and a ceramic.

17. The gas sensor as recited in claim 15, wherein the second cavities open into at least one of the delimiting surfaces of the sensor body, which are provided for penetration of molecules of a gas that is to be detected.

18. The gas sensor as recited in claim 15, wherein the size of the second cavities in at least one direction of extent is at least twice as great as the average size of the first cavities.

19. The gas sensor as recited in claim 18, wherein the size of the second cavities in at least one direction of extent is at least five times greater than the average size of the first cavities.

20. The gas sensor as recited in claim 19, wherein the size of the second cavities in at least one direction of extent is at least ten times greater than the average size of the first cavities.

21. The gas sensor as recited in claim 15, wherein the size of the first cavities is at least twice as great as the size of the molecules of the gas to be detected.

22. The gas sensor as recited in claim 15, wherein the size of the second cavities is at least five times greater than the size of the molecules of the gas to be detected.

23. The gas sensor as recited in claim 15, wherein the size of the first cavities in at least one direction of extent is greater than 0.5 nm.

24. The gas sensor as recited in claim 15, wherein the size of the second cavities in at least one direction of extent is greater than 2.5 nm.

25. The gas sensor as recited in claim 15, wherein the extent of the second cavities in at least one direction amounts to at least 50% of the layer thickness of the sensor body.

26. The gas sensor as recited in claim 15, wherein the second cavities form an open-pored spongy structure.

27. The gas sensor as recited in claim 15, further comprising:
an insulation layer situated between the electrodes in addition to the sensor body.

28. The gas sensor as recited in claim 15, further comprising:
at least one of: a temperature sensor, a heating element and a cooling element integrated into the gas sensor.

29. A method for manufacturing a gas sensor, comprising:
applying a first electrode to a substrate;
applying a sensor body to the first electrode, the sensor body including a gas-sensitive material which changes at least one physical parameter depending on the distribution density of a penetrating gas prevailing therein, and the sensor body having first cavities;
applying a second electrode; and
treating the sensor body to produce second cavities, wherein the material of the sensor body is acted upon by a space-demanding, finely divided or dissolved substance which is subsequently removed by dissolving, etching, vaporizing or diffusion, wherein the space-demanding, finely divided or dissolved substance is converted by dissolving, etching, vaporization or diffusion with another chemical substance before being removed, and wherein the space-demanding, finely divided or dissolved substance is thermally decomposed at elevated temperatures.

30. The method as recited in claim 29 wherein the second electrode is applied after treating the sensor body to produce the second cavities.

31. The method as recited in claim 29, wherein the second cavities are caused by different measures or physical effects than the first cavities in the manufacture of the sensor body.

32. The method as recited in claim 29, wherein the second cavities are created by a thermal treatment of the sensor body.

33. The method as recited in claim 32, wherein the thermal treatment includes at least one of: sudden temperature changes and great temperature differences which produce cracks in the sensor body.

34. The method as recited in claim 29, wherein the sensor body is manufactured by a sol-gel technique.

35. The method as recited in claim 29, wherein the sensor body is embrittled by temperature treatment or by irradiation with electromagnetic radiation or particulate radiation and then is exposed to a mechanical stress to produce cracks.

36. The method as recited in claim 29, wherein the second cavities have at least one of: a different shape from the first cavities and a different size that is larger in at least one direction of extent on the average in comparison with an average size of the first cavities.

37. The method as recited in claim 29, wherein the second cavities are caused by different measures or physical effects than the first cavities during the production of the sensor body.

38. A method for manufacturing a gas sensor, comprising:
applying a first electrode to a substrate;

applying a sensor body to the first electrode, the sensor body including a gas-sensitive material which changes at least one physical parameter depending on the distribution density of a penetrating gas prevailing therein, and the sensor body having first cavities;

applying a second electrode; and treating the sensor body to produce second cavities, wherein parts of the sensor body are removed by bombardment with electromagnetic or particulate radiation directly to create second cavities.

39. A method for manufacturing a gas sensor, comprising:

applying a first electrode to a substrate;

applying a sensor body the first electrode, the sensor body including a gas-sensitive material which changes at least one physical parameter depending on the distribution density of a penetrating gas prevailing therein, and the sensor body having first cavities;

applying a second electrode; and treating the sensor body to produce second cavities, wherein the sensor body is made by foaming a material already having pores.

40. A method for manufacturing a gas sensor, comprising:

applying a first electrode to a substrate;

applying a sensor body to the first electrode, the sensor body including a gas-sensitive material which changes at least one physical parameter depending on the distribution density of a penetrating gas prevailing therein, and the sensor body having first cavities;

applying a second electrode; and treating the sensor body to produce second cavities, wherein the sensor body is manufactured by pressing or sintering particles of a material already having pores.

* * * * *